(12) United States Patent
Schurr et al.

(10) Patent No.: US 8,192,349 B2
(45) Date of Patent: Jun. 5, 2012

(54) MEDICAL DEVICE FOR CHANGING THE SHAPE OF HOLLOW ORGANS IN THE HUMAN

(75) Inventors: Marc Oliver Schurr, Tubingen (DE); Chi-Nghia Ho, Tubingen (DE)

(73) Assignee: Ovesco Endoscopy AG, Tubingen (DE)

( * ) Notice: Subject to any disclaimer, the term of this patent is extended or adjusted under 35 U.S.C. 154(b) by 596 days.

(21) Appl. No.: 11/433,612

(22) Filed: May 12, 2006

(65) Prior Publication Data
US 2006/0264984 A1 Nov. 23, 2006

(30) Foreign Application Priority Data
May 13, 2005 (DE) .......................... 10 2005 007 597
Aug. 30, 2005 (DE) .......................... 10 2005 041 093

(51) Int. Cl.
*A61F 2/00* (2006.01)

(52) U.S. Cl. ........................................ 600/37; 606/151
(58) Field of Classification Search .............. 600/29–30, 600/37
See application file for complete search history.

(56) References Cited

U.S. PATENT DOCUMENTS

| 6,432,040 | B1 * | 8/2002 | Meah .............................. 600/37 |
| 7,152,607 | B2 * | 12/2006 | Stack et al. .................... 128/898 |
| 2002/0055750 | A1 * | 5/2002 | Durgin et al. ................. 606/151 |
| 2004/0092892 | A1 * | 5/2004 | Kagan et al. ................... 604/264 |
| 2004/0107004 | A1 | 6/2004 | Levine et al. |
| 2004/0147942 | A1 | 7/2004 | Chao |
| 2005/0192629 | A1 * | 9/2005 | Saadat et al. .................. 606/221 |
| 2005/0283235 | A1 * | 12/2005 | Kugler et al. ............. 623/14.13 |

FOREIGN PATENT DOCUMENTS

| DE | 101 59 470 | 6/2003 |
| WO | WO-01/35832 | 5/2001 |
| WO | WO-2004/087014 | 10/2004 |

* cited by examiner

*Primary Examiner* — John Lacyk
*Assistant Examiner* — Carrie R Dorna
(74) *Attorney, Agent, or Firm* — AlbertDhand LLP

(57) ABSTRACT

The present invention relates to a medical device for changing the shape of hollow organs in the human body, comprising at least one issue clamp, clip or anchor, which can be fixed to the organ tissue by means of a clamping or hooking-in action in order to provide a fixation point or a point of transmission of force in the organ. The clip or anchor has a receiving-element portion or hooking-in device for a flexible band, wire or tube, by means of which a force causing the change in shape can be applied to the organ at least partially via the clip.

10 Claims, 9 Drawing Sheets

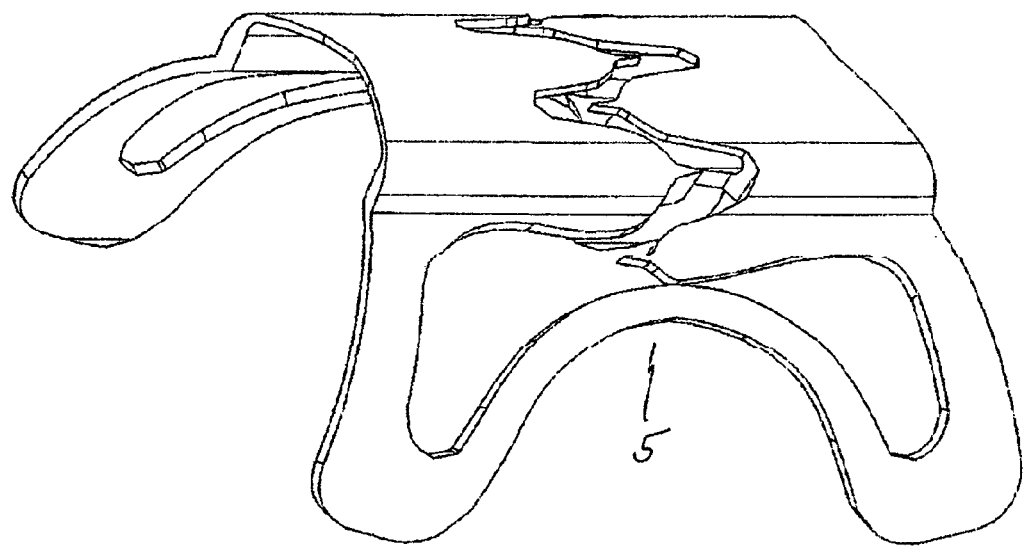
fig. 2

MEDICAL DEVICE FOR CHANGING THE SHAPE OF HOLLOW ORGANS IN THE HUMAN

TECHNICAL FIELD

The present invention relates to a medical device for changing the shape of hollow organs in the human body, for example of the digestive tract, and of the stomach in particular, according to the preamble of patent claim 1.

BACKGROUND OF THE INVENTION

Obesity (adiposity) is a present day civilization problem, which only in the rarest of cases is caused by hormonal diseases. In most cases wrong eating habits, lack of exercise, high-calorie food etc. are the main causes for obesity. Diets may promise a temporary and fast reduction in body fat but they condition a certain discipline of the respective patient as well as a constant monitoring by trained experts.

Here it must be pointed out that experience has shown that exactly such eating habits which lead to obesity are due to an undisciplined eating behavior of the respective patient. For this reason those patients are often not able to strictly follow the diets, or the patients return to their former eating habits after termination of the diet. In most cases conventional diets do in practice not lead to the desired results.

According to the prior art it has been known that these problems can be solved by reducing the size of certain sections of the digestive tract, in particular of the stomach, by means of a surgical operation, and to create a short-circuit connection to the small intestine. Thus the patient experiences a feeling of satiety even after having eaten even small food portions, which will then prevent him from taking more food, and thus the patient will lose weight. Here the methods shortly described in the following have become generally accepted for changing the shape and size of the respective organ in the human body:

1. According to one method this is achieved in a way that the size of the respective organ, for example of the stomach, is reduced by isolating a part of the stomach from the other part by staples or sutures and directly connecting it to the small intestine. Although this method leads to a long-lasting success in combating obesity, it proves disadvantageous inasmuch as said operation is irreversible and entails considerable strain for the patient.
2. According to another method this is achieved by creating a partitioning of the stomach by applying a gastric band from the outside. Thus a kind of "pre-stomach" is created, which is rather quickly filled with food, and this will much faster lead to a feeling of satiety.
3. Also in cases of treatment for other diseases of the digestive tract, for example in case of esophagus reflux disease, changing the lumen of the hollow organ plays an important part. In case of fundoplication, for example, the entrance to the stomach is supported from the outside by a tissue sleeve or an artificial implant.

DISCLOSURE OF THE INVENTION

Based on this prior art it is the object of the present invention to create a device for changing the shape of hollow organ in the human body, which can be applied in a way that causes as little as possible strain for the patient and, which furthermore maintains the natural functions of the respective organ as far as possible.

BRIEF DESCRIPTION OF THE DRAWINGS

FIG. 2 shows an enlarged illustration of the first version of a tissue clamp or clip as applied in a device according to FIG. 1, FIGS. 3 and 4 are applied.

DETAILED DESCRIPTION OF SPECIFIC EMBODIMENTS OF THE INVENTION

Figure 1:
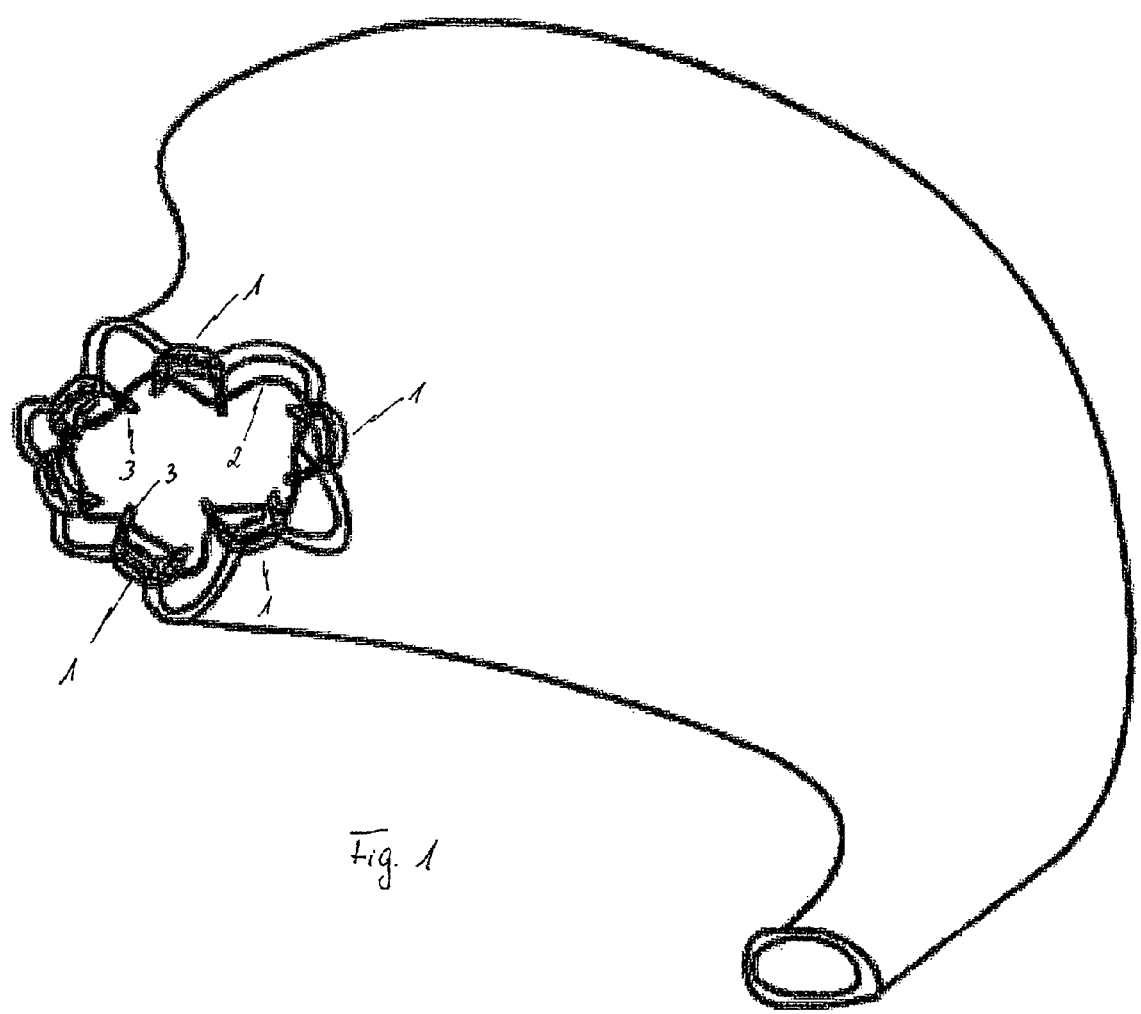
FIG. 1 shows a general illustration of a medical device according to a first preferred embodiment of the invention.
Figure 1A:
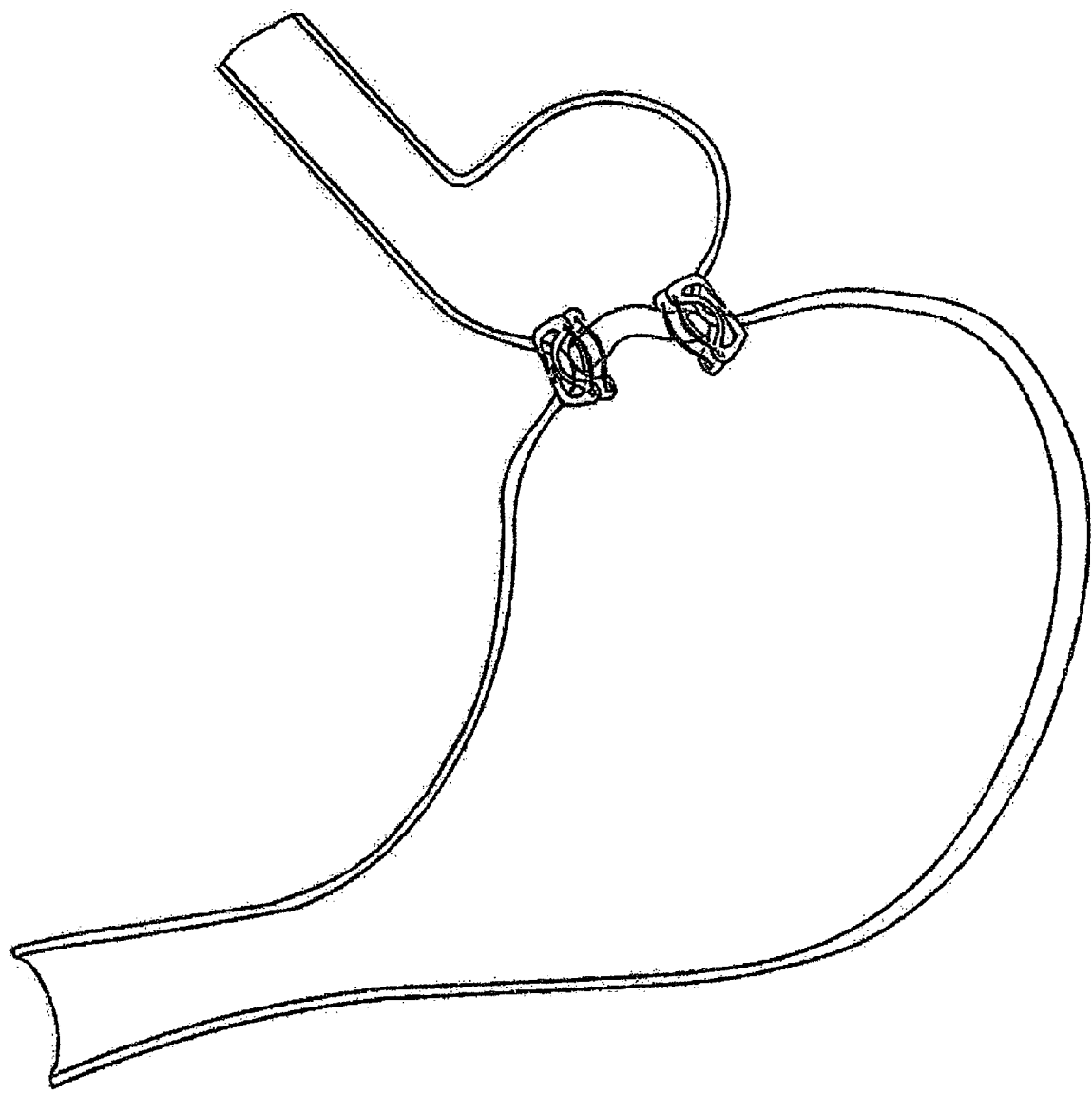
Figure 16:
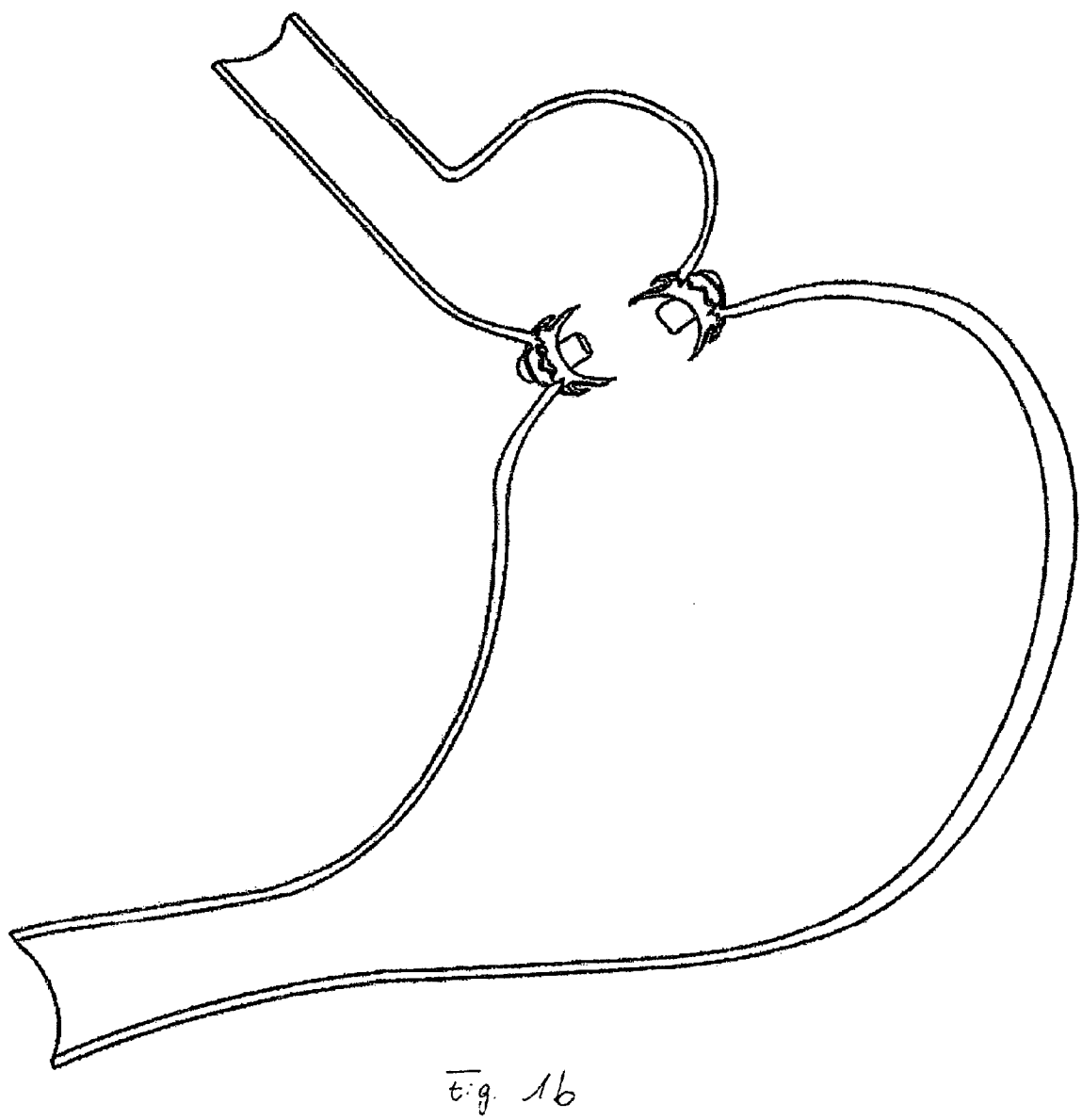

In FIG. 1 the functioning of a medical device according to the first preferred embodiment of the invention is illustrated.

It shows that the medical device comprises as main parts a certain number of tissue clamps 1, clips or anchors, as well as a preferably flexible or elastic band 2, wire or tube, along which the clips 1 or anchors are aligned.

For this purpose each clip or anchor has a kind of eyelet or hole 3, through which the band 2 is threaded. Alternatively each clip 1 or anchor can comprise a detachable hooking-in device being a shackle, a hook or similar (not illustrated), by means of which the clip 1 can be attached to the band 2. In a further preferred embodiment this hooking-in device can be formed in a way that the clip 1 or the anchor can be moved along the band 2.

According to one preferred embodiment the band 2 shown in FIG. 1 is preferably made from a biocompatible (body-friendly) and flexible material like nylon, which can be tied or bonded at its loose ends or can be tied to a closed ring or loop by means of a closing mechanism (not illustrated) is preferably formed in a way that the diameter of the closed ring or loop can be changed and freely adjusted as it is done with a belt buckle.

Instead of the flexible band 2 it is also possible to use a flexible wire or a spring wire preferably in combination with the closing mechanism described above. It is also possible to apply as an alternative an inflatable, flexible and, if applicable, elastic tube, which is formed to an open or closed ring or loop, and which can be inflated with a gas, or a preferably body-friendly fluid like saline solution or just water, thus enabling the reduction/extension of the ring or loop diameter described by the tube.

Figure 3:
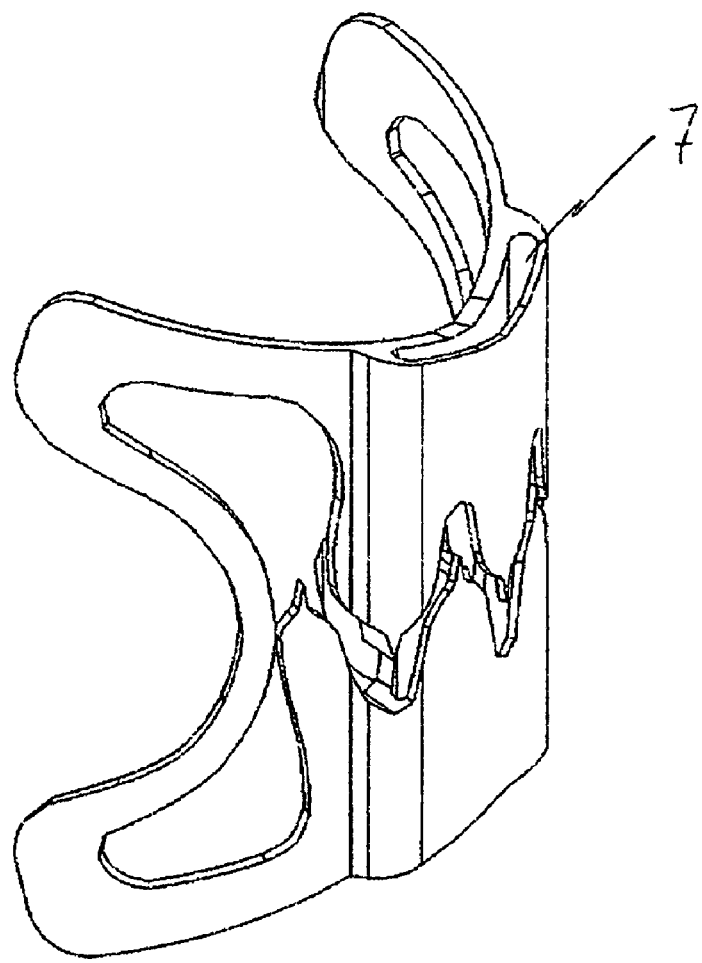
FIG. 3 shows an enlarged illustration of the second version of the tissue clamp or clip as applied to a device according to FIG. 1.
Figure 4:
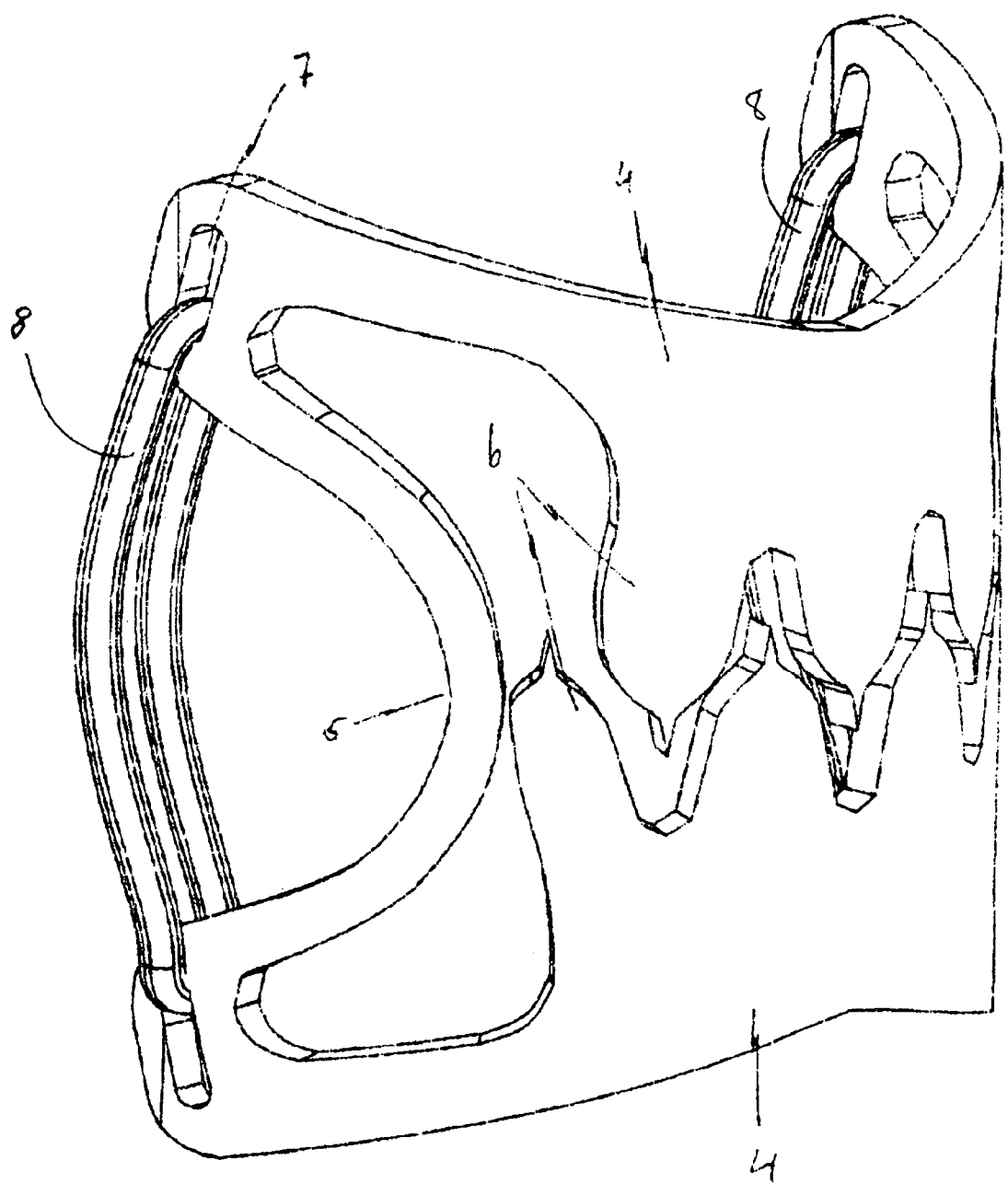
FIG. 4 shows an enlarged illustration of the third version of the tissue clamp or clip as applied to a device according to FIG. 1.

The following individual clip constructions are further specified referring to FIGS. 2 to 4.

Clip 1 according to FIG. 2 is prior art as far as its general construction is concerned and has already been known, for example, from document WO 01/35832 from the same applicant, the disclosure of which is herein included in the content of this application.

According to this clip 1 comprises a mouth-like clamping device with two toothed jaws 4, which can be opened and closed by means of two lateral joints or flexible recesses 5 respectively. The joints or the flexible recesses 5 are preferably made from spring elastic bands, which memorize a spring energy when opening the jaws 4; this, after release of the jaws 4. i.e. when the joints or flexible recesses 5 are activated, leads to a snap closing of the jaws 4 with a predetermined clamping force.

Each clip 1 is punched in one place from a spring steel sheet in a way that a ring with partially different ring widths is worked from the spring steel sheet. Two diametrically opposite rings sections with wide ring widths form the two jaws 4, whereas the two ring sections in between with small ring widths form the joints or the flexible recesses 5 respectively. The jaws 4 are formed by bending the ring sections with wide ring widths to an arch and at the same time twisting (distorting) the two ring sections with small ring widths by 90° about their longitudinal axis in order to form the joints. This permanent formation of the punched spring steel sheet results in a kind of shark's mouth having two rows of teeth which are formed by punching the rings sections with wide ring widths, and which move towards each other.

Here it must be pointed out that the construction of the clip 1 according to FIG. 1 may differ from the above description. Therefore it is also possible to form the two jaws 4 separately and connect these by means of two lateral joints with joint pins. The pretension force required for the clamping action, or the snap closing of the two jaws 4 respectively, can in this case be generated by means of an external spring device (not illustrated) arranged in the vicinity of the two joints 5. It is also possible to provide for an additional closing mechanism instead of the device creating a pretension force as illustrated in FIG. 1, which locks the two jaws in closed position. In this case the clamping force would have to be applied to the two jaws 4 externally by means of a suitable tool activating the closing mechanism, so that the tool could be removed again afterwards.

An essential construction feature of the above describe clip 1 or anchor according to FIG. 1 consists in the hooking-in device briefly mentioned above for connecting the clip/anchor 1 to the band 2, wire or tube.

In the simplest embodiment this hooking-in device consists in the feed-through hole 3 (see FIG. 2) in the jaw 4, or in an eyelet 7 (see FIG. 3), which is additionally formed when punching the clip 1 or producing the anchor, and through which the band 2, wire or tube is threaded. Also the recess itself formed between joint 5 and jaw 4 can be used as eyelet. Alternatively it is also possible to additionally equip the clip 1 or anchor to the already closed ring of the band 2, wire or tube. In this case the hooking-in Levine can, for example, be a snap-in hook or similar, which is, for example, fixed to the clip 1 or the anchor in the aforementioned feed-through hole 3 or eyelet. It is also possible that parts of the clip 1 or the anchor, in particular the joints 5 or the flexible recesses of the clip 1 are constructed in a way that they form a hooking-in device. This could, for example, be achieved by a spiral or loop-shaped formation of the joint 5 or the flexible recess, which naturally results in a basically closed feed-through opening for holding the band or another detachable hooking-in device.

The functioning of the aforementioned medical device can be described as follows:

As explained above an endoscopic implantation of a medical device represents the most tolerable operation for the patient. In this case the medical device must be fixed to the hollow organ from its inside. As shown in FIG. 1 a certain number of the tissue clamps 1, clips or anchors as described above are therefore introduced into the hollow organ by means of a non-illustrated endoscope and placed in predetermined positions at the inside of the organ. For this purpose each individual clip 1 or anchor is moved close to the organ tissue and the pretension spring for clamping the clip 1 or expanding the anchor is released. This then clamps or holds a tissue fold between its jaws 4 or its hooks or pins with a predetermined champing or expansion force and thus the teeth 6, hook, pins or points of each jaw 4 cut into the tissue and preferably perforate it. Thus each clip 1 or anchor is fixed to the inside of the organ at a certain distance to each other and thus creates a point of application for a tension force in the organ tissue.

Specific Mode for Carrying Out the Invention

Then the band 2, wire or tube is attached to the hooking-in device of each clip or anchor, i.e. the band, wire or tube is fed through the feed-through hole/eyelet 7 of each clip or anchor, or the clip is attached to the band, wire or tube by means of the detachable additional hooking-in device.

Finally the ring or loop diameter described by the band, wire or tube is reduced, in case of the band or the wire this is done by drawing the loose ends. In case of a tube this is deflated or inflate, which will change the diameter of the tube formed to a ring or a loop.

By reducing the ring or loop diameter a tension force is applied to the clips or anchors fixed in the organ tissue, which, as a consequence of drawing the band, wire or tube, then leads to a constriction of the organ in the respective cross-sectional area.

By means of the device described above as well as the herewith related functions the following advantages result as against the prior art:

As already specified the device can be inserted into the organ by means of endoscopy, if required supported by instruments through a surgical port from the outside of the organ, and represents thus little strain on the patient.

Since the points of application of the force are not effected by means of sutures but by means of tissue clamp/clip/anchor the installation of the device can be realized within a short period of time, which has a favorable effect on the patient's well-being as well as on the treatment expenses.

The device can be formed in a way that the installation is reversible, i.e. it can be removed without any problem and thus the respective organ can be restored to its original shape and size.

If the device is applied in order to reduce the volume of the stomach, the internal band, wire or tube has the additional effect of being a kind of flow resistance. This means that the internal band, wire or tube holds back food eaten and therefore food accumulates above the device and thus effected constriction of the stomach. Therefore the patient quickly experiences a feeling of satiety, so that the total quantity of food taken per portion is reduced. If the device is applied in order to reduce reflux from the stomach into the esophagus the respective band has the function of reducing the reflux of stomach content into the esophagus by supporting the gastric wall in the vicinity of the entrance to the stomach.

FIGS. 2 to 4 show different versions of a clip 1 according to the invention with different rows of teeth and spring pretensions.

In particular clip 1 shown in FIG. 4 is equipped with an additional pretension device 8 being an elastic strip which pretensions the two jaws 4 in the opening direction. The other parts of the construction of the clip 1 according to FIG. 4 correspond to the one of the clip according to FIG. 2.

The additional pretension device 8 has the function of automatically maintaining the clip 1 in an open position, and the closing force of the joints 5 does not press the jaws into effective closing position until the snapping motion of the jaws has exceeded a threshold value.

Figure 5:
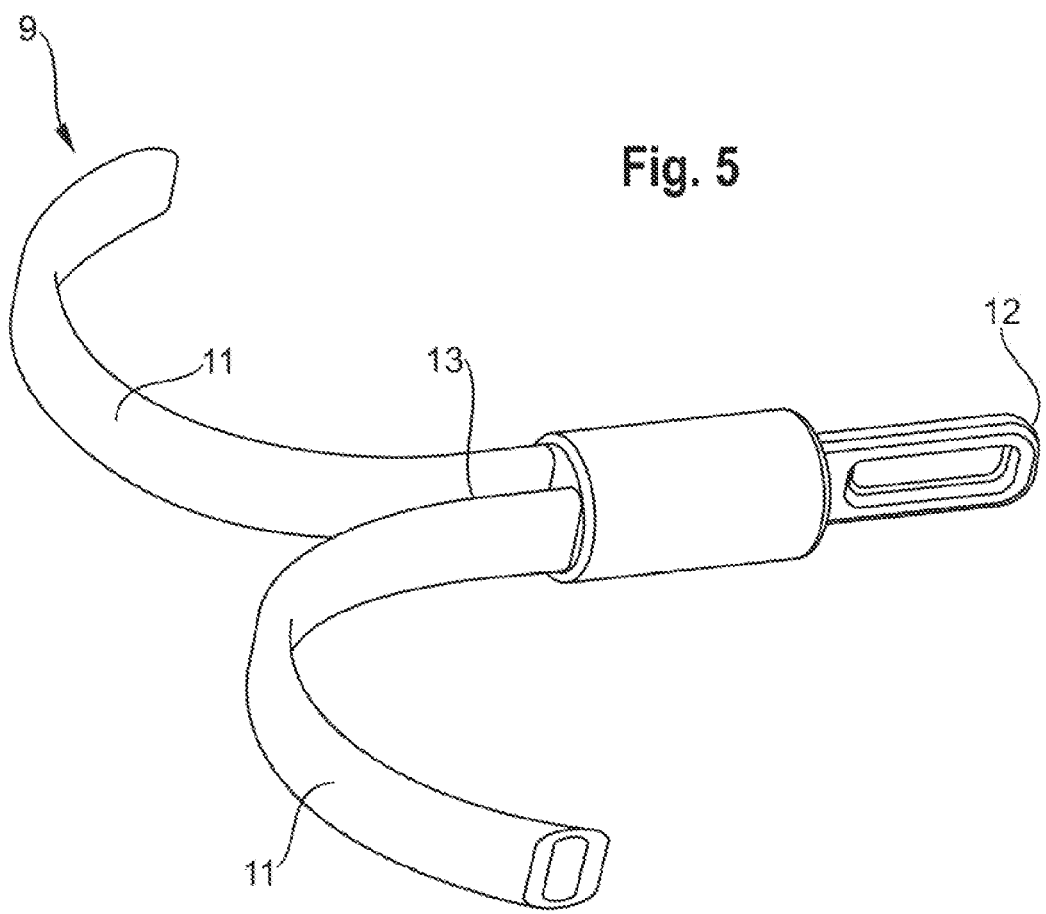
FIG. 5 shows an enlarged illustration of the first version of a tension anchor being an alternative to a tissue clamp or clip, as applied to a device according to FIG. 1.
Figure 6:
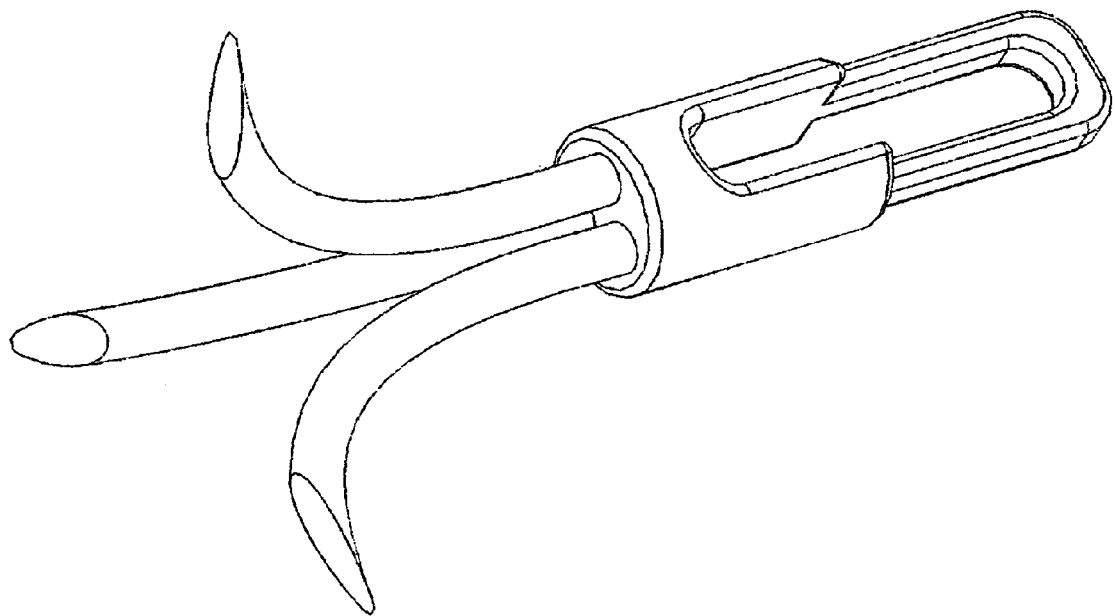
FIG. 6 shows an enlarged illustration of the second version of a tension anchor being an alternative to a tissue clamp or clip, as applied to a device according to FIG. 1, and FIG. 7 show a general illustration of the medical device according to the first preferred embodiment of the invention, where the different clips as per

FIGS. 5 and 6 show tension anchors, which are basically prior art and are known, for example, from document DE 10159470 of the same applicant, the disclosure of which is herewith included in the content of this application, and which represent alternative construction of the clip 1 according to the invention, mainly mainly comprising a certain number of hooks 9 and a preferably eyelet-shaped hooking-in device 10 for the band, wire or tube.

According to FIG. 5 the hook 9 consists of two arched arms 11, which are combined in one end of a base 12. Preferably the bent arms 11 are formed as tubes and the inner longitudinal channel 13 opens to the outside at the loose ends of the arms 11 in order to hold the band 2 and the band can be fed through. According to FIG. 7 the hook 9 has, in contrast to the hook according to FIG. 5, three arched arms 11 which in this case, however, are made from solid material.

Figure 7:
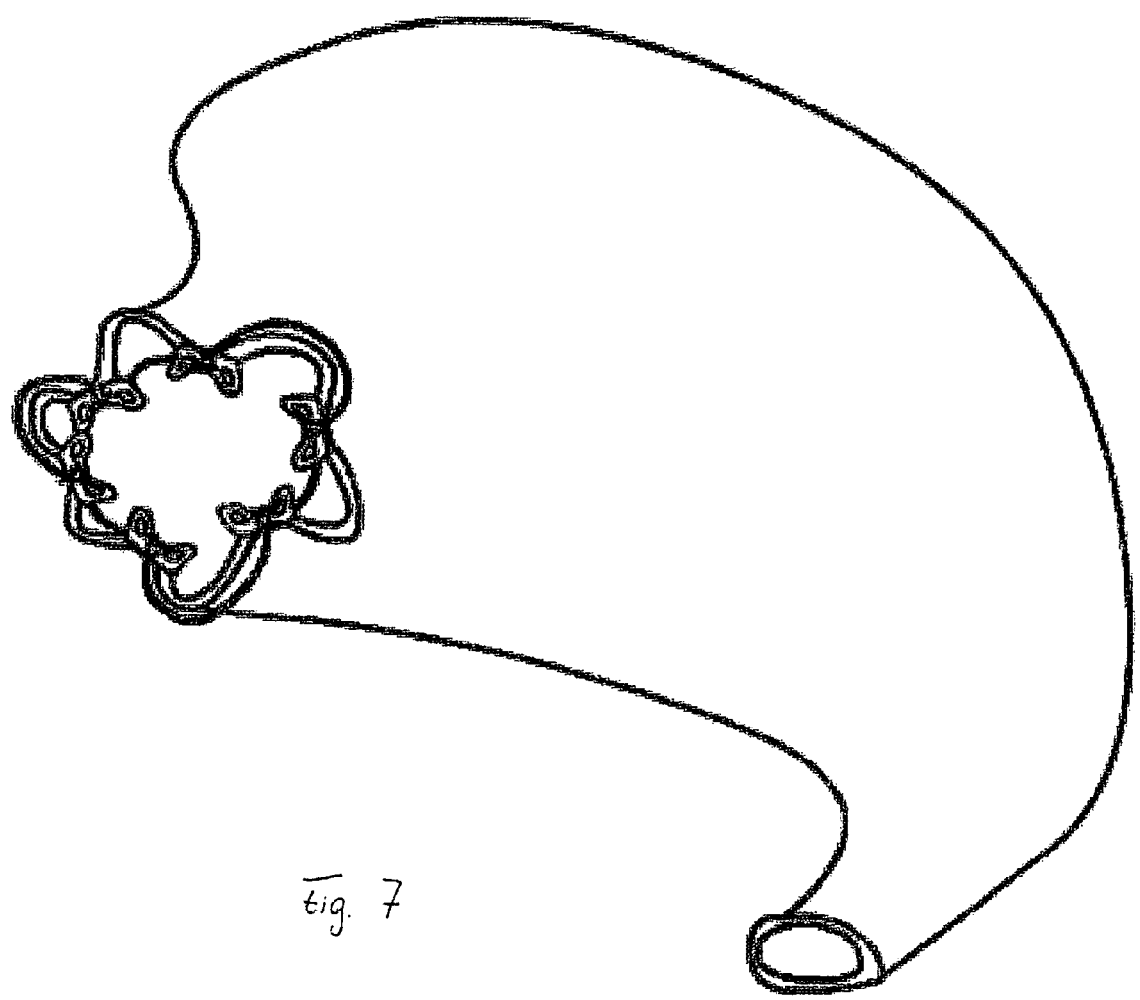

FIG. 7 shows the medical device according to the first embodiment using the clips according to FIGS. 2 and 4. In this particular application of the medical device two diametrically positioned clips are provided and are affixed to the organ wall from the inside of the organ. The band is attached to the respective eyelets/feed through holes of the clips and passes straight through the cavity of the organ.

The advantage of this alignment of the band lies in the fact that thus a kind of flow resistance is created which prevents food eaten from passing through the organ too fast. This means that the band is aligned in such a way that it effects an accumulation of the food and thus the patient is quicker to experience a feeling of satiety.

Also in a second embodiment the medical device according to the invention comprises a certain number of tissue clamps 1 or clips or anchors and a band, wire or tube 2, along which the clips 1 or anchors are aligned. In this case, however, the clips 1 or anchors are not formed as tension anchors, but merely as position fixtures. In principle the constructive realization of the clamps 1 according to the second embodiment corresponds to the one described in the above mentioned embodiment. However, the second embodiment provides that the band 2, wire or tube is an open ring or loop, and that at one end of the band 2, wire or tube there is a needle (not illustrated). This needle not only serves to facilitate the feeding of the band 2, wire or tube through the holes/eyelets 3 of the clamps 1, but also to pierce through the wall of the organ.

In this case the band 2, wire or tube is by endoscopic means fed through the respective eyelet 3 and then pierced from the inside of the organ through the wall of the organ in the dose vicinity of each clip 1 and laid around the organ on its outside to reach the next clip 1 or anchor. Then the band 2, wire or tube is again pierced through the wall of the organ back to the inside and again fed through at the respective clip 1. When drawing the two loose ends of the band 2, wire or tube and consecutive fixing (by means of a knot, bond or a fixing device like a damp socket) a radially uniform pressure is applied to the outside of the organ similar to the one effected by a sleeve, which effects a constriction of the organ. Here the band can be led alternatively at the outside and the inside of the organ, as is shown in FIG. 9, or surround the organ almost completely from the outside, as is pointed out in FIG. 10. In this case the band 2, wire or tube is by endoscopic means fed through the respective eyelet 3 and then pierced from the inside of the organ through the wall of the organ in the close vicinity of each clip 1 and laid around the organ on its outside to reach the next clip 1 or anchor. Then the band 2, wire or tube is again pierced through the wall of the organ back to the inside and again fed through at the respective clip 1. When drawing the two loose ends of the band 2, wire or tube and consecutive fixing (by means of a knot, bond or a fixing device like a damp socket) a radially uniform pressure is applied to the outside of the organ similar to the one effected by a sleeve, which effects a constriction of the organ. Here the band can be led alternatively at the outside and the inside of the organ.

In both cases the clamps 1 merely have the function to prevent the slipping of the band 2, wire or tube and thus to maintain the exact constriction position. Therefore the pretension force applied to the two jaws 4 of the clip 1 or respectively to the hooks of the anchor can be much lower than compared to the one of the first embodiment, and thus the spring device itself can also be much smaller. The advantage of this second embodiment of the medical device as compared to the first embodiment lies in the following effects:

The mechanical strain on the organ tissue at the fixing points is lower because of the lower clamping force required of the clip or respectively the lower expansion force required of the anchor.

The constriction force is not applied in certain points as according to the first embodiment but linearly distributed. This leads to a more homogeneous distribution of the force.

According to one version of the second embodiment described above the modified medical device according to the invention comprises a certain number of tissue clamps, clips or anchors and a band, wire or tube along which the clips or anchors are aligned. In this case the clips or anchors serve as position fixtures as according to the second embodiment. In principle the constructional realization of the clamps according to the modification corresponds to the one described above in the second embodiment. It is, whoever, provided in this modification of this second embodiment that the band, wire or tube is an open ring or loop.

In this case the clips or anchors are placed endoscopically in the respective positions from the inside of the organ, and the band, wire or tube is fed from the outside of the organ by laparoscopic, minimally invasive or open surgery, through the ring-shaped eyelets of the clips or the anchors which have completely perforated the wall of the organ. This means that in this case the eyelets or feed-through holes are placed in a section of the clip which is, after the clip has been fixed to the wall of the organ, positioned at the outside of the organ.

When drawing the two loose ends of the band 2, wire or tube and consecutive fixing (by means of a knot, bond or a fixing device like a clamp socket) a radially uniform pressure is applied to the outside of the organ similar to the one effected by a sleeve, which effects a constriction of the organ.

Also in this case the clamps or anchors merely have the function to prevent the slipping of the band, wire or tube and thus maintain the exact constriction position. Therefore the two jaws of the clip or the anchor have, in contrast to the first and second embodiment, a ring-shaped eyelet in the jaw (in particular in the teeth) or at the hooks, so that the band, wire or tube can be fed through. The advantage of this third embodiment of the medical device as compared to the first embodiment lies in the following effects:

The band, wire or tube is completely positioned at the outside of the organ and the constriction force can be radially applied to the organ in an even better way than according to the first or second embodiment. Thus the constriction force is more homogeneously applied to the outer wall of the organ.

By means of this device the surgeon has the additional possibility of a minimally invasive or open surgery. Thus this device can much better compress or respectively radially clamp the tissue between the clips or the anchors.

Finally it must be pointed out that the form of the clip or the anchor may vary depending on its purpose and place of application. Therefore various tooth, hook or needle shapes, the creation of an underbite or overbite of the two jaws, as well as various methods of fixing, like simple tissue clamping or a complete perforation of the wall of the organ, and interlocking of the teeth, hooks or needles can be provided. Also the material and coating of the clips or anchors and the band, wire or tube can be freely selected. For example each clip, anchor, band, wire or tube can be coated with a material that enhances intergrowth with the organ tissue so that a higher tension force can be applied to the organ tissue. Or alternatively the clip or the anchor, the band, the wire or the tube are made from a dissolvable material so that it is not necessary to remove the device after elapse of a predetermined period of time.

The present invention substantially relates to a medical device for changing the shape of hollow organs in the human body. This device comprises among other things a tissue clamp or clip, or alternatively an anchor, which can be fixed to the organ tissue by means of a clamping or interlocking in order to provide a fixation point or point of transmission of force at the organ. The clip comprise/forms a receiving element portion (pick-up) or mount for a flexible band, wire or tube by means of which a force causing the change of shape can be applied to the organ preferably via the clip.

Beside the described embodiments for the application of the device according to the invention at the stomach, also embodiments for the application in other sections of the digestive tract are possible, for example in the intestine.

Also in hollow organs other than the digestive tract the device according to the invention for changing the diameter or the shape can be applied. This relates, for example to the blood vessel system or the urinary passage.

What is claimed is:

1. A medical device for changing the shape of hollow organs in the human body comprising:
    at least one mouth-like organ tissue clamping clip comprising two toothed jaws that are pivotably connected to each other by joints or flexible recesses wherein the clip is punched in one piece from a spring steel sheet in a way that a ring with partially different ring widths is worked from the steel sheet wherein two diametrically opposite ring sections with wide widths form the two toothed jaws whereas two ring sections in between with small ring widths form the joints or the flexible recesses,
    one of a flexible band, wire or tube threaded through a receiving element portion or hooking-in device configured as a through-hole in at least one toothed jaw having the wide width, wherein the through-hole is formed in the material of the clip when punching the clip, and by means of which a force causing a change of shape can be applied to the organ at least partially via the clip.

2. A medical device according to claim 1, wherein each jaw comprises teeth, hooks or needles and wherein the teeth, hooks or needles of the jaw are arranged between the joints or flexible recesses.

3. A medical device according to claim 2, wherein the teeth, hooks or needles of the jaws comprise corresponding profiles that can be interlocked with each other.

4. A medical device according to claim 1, wherein the flexible band, wire or tube is made from an expandable or an elastic material.

5. A medical device according to claim 1, wherein the band, wire or tube is made from a metal, a shape memory alloy or a plastic.

6. A medical device according to claim 1, wherein in case a tube is provided the tube can be inflated or deflated with a biocompatible fluid by means of a connecting device.

7. A medical device according to claim 1, wherein the band, wire or tube is formed to an open or closed ring or loop, wherein in case of an open ring or loop, two loose ends of the band, wire or tube can be connected to each other by means of a closing mechanism which enables the adjustment of a diameter of the ring or loop.

8. A medical device according to claim 1, wherein the band, wire or tube is provided with a needle at one loose end.

9. A medical device according to claim 1, wherein the clip and the band, wire or tube are provided with a coating that enhances or inhibits intergrowth with an organ tissue.

10. A medical device according to claim 1, wherein the clip, band, wire or tube are made from a material that dissolves in the body after elapse of a predetermined period of time.

\* \* \* \* \*